United States Patent [19]
Tanner et al.

[11] Patent Number: 5,827,508
[45] Date of Patent: Oct. 27, 1998

[54] STABLE PHOTOPROTECTIVE COMPOSITIONS

[75] Inventors: Paul Robert Tanner, Maineville; Patricia Ritenour Hertz, Hamilton; Margaret Ann O'Donoghue, Monroe; Christopher Irwin, Cincinnati, all of Ohio

[73] Assignee: The Procter & Gamble Company, Cincinnati, Ohio

[21] Appl. No.: 714,483

[22] Filed: Sep. 27, 1996

[51] Int. Cl.$^6$ .............................. A61K 7/42; A61K 7/00; C01G 9/00; C09C 1/04
[52] U.S. Cl. ........................ 424/59; 106/425; 423/622; 424/60; 424/400; 424/401
[58] Field of Search ............................... 424/89, 60, 400, 424/401; 423/622; 106/425

[56] References Cited

U.S. PATENT DOCUMENTS

| | | | |
|---|---|---|---|
| 4,387,089 | 6/1983 | DePolo | 424/59 |
| 4,489,057 | 12/1984 | Welters | 424/47 |
| 4,937,370 | 6/1990 | Sabatelli | 560/45 |
| 4,999,186 | 3/1991 | Sabetelli | 424/60 |
| 5,041,282 | 8/1991 | Sabatelli | 424/59 |
| 5,138,089 | 8/1992 | Sabatelli | 560/50 |
| 5,160,731 | 11/1992 | Sabatelli | 424/59 |
| 5,372,805 | 12/1994 | Finkel et al. | 424/59 |
| 5,486,631 | 1/1996 | Mitchnick | 556/10 |

FOREIGN PATENT DOCUMENTS

| | | | |
|---|---|---|---|
| 0 303 995 A | 2/1989 | European Pat. Off. | A61K 7/42 |
| 0 619 999 A | 10/1994 | European Pat. Off. | A61K 7/42 |
| 94/04131 | 3/1994 | WIPO | A61K 7/42 |
| 94/15580 | 7/1994 | WIPO | A61K 7/42 |

OTHER PUBLICATIONS

Derwent Publications Abstract No. 97–037960; Nov. 12, 1996; JP 08295 620.
Merck Index, Tenth Edition, 1983, p. 1457 entry 9952.
International Cosmetic Ingredient Dictionary, Fifth Edition, 1993, pp. 788–789.
Z–COTE HP1 brochure, sunSmart, inc., Jul. 1, 1994.

*Primary Examiner*—Shelley A. Dodson
*Attorney, Agent, or Firm*—Loretta J. Henderson; George W. Allen; David L. Suter

[57] ABSTRACT

The present invention relates to compositions which are useful for providing protection to the skin of humans from the harmful effects of ultraviolet radiation. In particular the present invention relates to compositions having improved chemical, physical, and photostability. These compositions comprise from about 0.1% to about 10% of a dibenzoylmethane sunscreen compound, from about 0.1% to about 20% of a surface-treated zinc oxide, and a carrier suitable for application to the skin.

9 Claims, No Drawings

STABLE PHOTOPROTECTIVE COMPOSITIONS

TECHNICAL FIELD

The present invention relates to compositions which are useful for providing protection to the skin of humans from the harmful effects of ultraviolet radiation. In particular the present invention relates to compositions having improved chemical, physical, and photostability. These compositions comprise from about 0.1% to about 10% of a dibenzoylmethane sunscreen compound, from about 0.1% to about 20% of a surface treated zinc oxide, and a carrier suitable for application to the skin.

BACKGROUND OF THE INVENTION

The damaging effects of sunlight on skin are well documented. Contrary to what most people believe, it is not necessary that one sunbathe to suffer the ill-effects of excessive UV exposure. In fact, significant damage can be done just by routine day to day activities in sunlight. The major short term hazard of prolonged exposure to sunlight is erythema, i.e. sunburn. In addition to the short term hazard are long term hazards such as malignant changes in the skin surface. Numerous epidemiologic studies demonstrate a strong relationship between sunlight exposure and human skin cancer. Another long term hazard of ultraviolet radiation is premature aging of the skin. This condition is characterized by wrinkling and pigment changes of the skin, along with other physical changes such as cracking, telangiectasis, solar dermatoses, ecchymoses, and loss of elasticity. The adverse effects associated with exposure to UV radiation are more fully discussed in DeSimone, "Sunscreen and Suntan Products," *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation," *International Journal of Cosmetic Science*, 4, pp. 15–24 (1982); and U.S. Pat. No. 4,387,089, DePolo, issued Jun. 7, 1983; all of these references being incorporated by reference herein in their entirety. Hence, although the immediate effects of ultraviolet radiation may be cosmetically and socially gratifying, the long term hazards are cumulative and potentially serious.

The fact that these effects are taken seriously by the general public is suggested by considering the sun protection product market. This market has grown considerably in recent years and many new products are introduced each year. What used to be looked upon as a seasonal business is no longer seen as such. Sunscreen agents are now included in a diversity of personal care products, particularly cosmetic type products which are worn on a daily basis.

Many conventional sunscreen compositions suffer from disadvantages such as providing inefficient UV protection, and from chemical physical and photo-instability. Most conventional sunscreening compounds are efficient at absorbing UV wavelengths in the 290–320 nm UVB region, but are less efficient at absorbing in the 320–400 nm UVA region. One solution to boosting the UV protection efficiency of sunscreen formulations is to utilize UVA absorbing sunscreen compounds in the formulations. Especially effective UVA absorbers are sunscreens containing the dibenzoylmethane chromophore. See U.S. Pat. No. 4,489,057, to Welters et al., issued Dec. 18, 1984, and U.S. Pat. No. 4,387,089, to DePolo, issued Jun. 7, 1983, which are both incorporated by reference herein in their entirety, and which both disclose dibenzoylmethane sunscreen agents. However, dibenzoylmethane sunscreen agents are difficult to formulate and often yield compositions lacking the desired chemical physical, and photo-stability. In particular, dibenoylmethane sunscreen compounds tend to photodegrade during UV exposure, thereby reducing their effectiveness.

Another attempted solution for providing improved photoprotection compositions is to incorporate physical sunblocks, i.e. inorganic compounds such as zinc oxide. However, these materials are not easily formulated into stable products. For example these materials tend to agglomerate in the finished formulations, thus losing their effectiveness and resulting in unacceptable aesthetic properties such as whitening and viscosity changes. Furthermore, materials such as zinc oxide are reactive materials which exhibit a wide range of reactivity with alkaline as well as acidic solutions, liquids, and gases.

The present invention utilizes a surface treated zinc oxide in combination with a dibenzoylmethane sunscreen compound. The resulting compositions demonstrate unexpected photostability, chemical stability, and physical stability, as well as providing good UVA protection. Without being limited by theory, it is believed that the surface treatment of the zinc oxide renders the zinc oxide less reactive to the dibenzoylmethane derivative and the other components in the composition, thereby resulting in less chemical and physical degradation of the composition.

Therefore, it is an object of the present invention to provide novel compositions for providing protection from the harmful effects of UV radiation to human skin.

It is a further object of the present invention to provide photoprotective compositions comprising a dibenzoylmethane sunscreen compound, a surface treated zinc oxide, and a carrier suitable for application to human skin.

It is a further object of the present invention to provide photoprotective compositions having good UV protection efficacy.

It is a further object of the present invention to provide photoprotective compositions which are chemically, physically, and photo-stable.

It is a further object of the present invention to provide methods for protecting human skin from the harmful effects of UV radiation.

These and other objects will become readily apparent from the detailed description which follows.

SUMMARY OF THE INVENTION

The present invention relates to photoprotective compositions having enhanced stability that are useful for protecting human skin from the harmful effects of UV radiation, comprising:

(a) from about 0.1% to about 10% of a dibenzoylmethane sunscreen compound, (b) from about 0.1% to about 20% of a surface-treated zinc oxide having a mean particle size diameter from about 0.01 microns to about 100 microns, and (c) a carrier suitable for application to human skin.

In further embodiments, the present invention relates to a photoprotective composition useful for providing protection to human skin from the harmful effects of ultraviolet radiation, said composition prior to mixing, comprising:

(a) from about 0.1% to about 10% of a dibenzoylmethane sunscreen compound, (b) from about 0.1% to about 20% of a surface-treated zinc oxide having a mean particle size diameter from about 0.01 microns to about 100 microns, and (c) a carrier suitable for application to human skin.

In yet further embodiments, the present invention also relates to methods for providing protection to human skin from the harmful effects of UV radiation.

All percentages and ratios used herein are by weight of the total composition. All measurements made are at 25° C., unless otherwise designated. All weight percentages, unless otherwise indicated, are on an actives weight basis. The invention hereof can comprise, consist or, or consist essentially or, the essential as well as optional ingredients and components described herein.

DETAILED DESCRIPTION OF THE INVENTION

The compositions of the present invention are useful for providing protection to human skin from the harmful effects of ultraviolet radiation and are useful for topical application to the human skin. These compositions can be formulated into a wide variety of product forms including lotions, creams, non-aerosol pump sprays, aerosol sprays, sticks, oils, gels, mousses, and the like. In addition to the essential components described herein, a variety of additional optional ingredients known in the art can also be used.

The term "topical application," as used herein, means to apply or spread the compositions to the surface of the skin.

The term "carrier suitable for application to human skin," as used herein, means that the carrier and its components are suitable for use in contact with human skin without undue toxicity, incompatibility, instability, allergic response, and the like. Such carriers are well-known to one of ordinary skill in the art, and can include one or more compatible liquid or solid filler diluents or vehicles which are suitable for administration to human skin.

The compositions of the present invention have good UVA absorbing efficiency, i.e. they provide protection to human skin from the harmful effects of ultraviolet radiation without requiring undue amounts of the sunscreen actives. The compositions also demonstrate good chemical stability, physical stability, and photo-stability.

The term "chemical stability," as used herein, means that the various components of the compositions, especially the dibenzoylmethane sunscreen compound and the surface treated zinc oxide, do not exhibit appreciable breakdown or degradation. For example, the compositions of the present invention typically retain about 75% or more of the initially added dibenzoylmethane over about a three month period of time at room temperature.

The term "physical stability," as used herein, means that the overall composition exhibits physical characteristics such as resistance to developing off-odors and resistance to discoloration and darkening. The term is further used herein to refer to maintenance of viscosity, resistance to syneresis, and in the case of emulsions, resistance to phase separation. For example, the compositions of the present invention typically maintain their physical stability for at least about a three month period of time at room temperature.

The term "photo-stability," as used herein, means that the various components of the compositions, especially the dibenzoylmethane sunscreen compound and the surface treated zinc oxide do not exhibit appreciable breakdown or degradation upon exposure to ultraviolet radiation. For example, the compositions of the present invention typically retain about 75% or more of the initially added dibenzoylmethane sunscreen compound when exposed to about 5 to about 10 Joules of UV radiation from a xenon arc solar simulator, configured and filtered, as known by one of ordinary skill in the art, to primarily emit wavelengths from about 290 nm to about 400 nm.

The terms "chemical stability," "physical stability," and "photo-stability" have been separately defined herein for convenience. Nevertheless, it is realized that these stability phenomena are not necessarily distinct and that chemical stability, physical stability, and photostability can each effect the other.

The compositions of the present invention comprise the following essential components.

Dibenzoylmethane Sunscreen Compound

The compositions of the present invention comprise from about 0.1% to about 10%, more preferably from about 0.25% to about 7.5%, and most preferably from about 0.5% to about 3%, by weight of the composition, of a dibenzoylmethane sunscreen compound. Mixtures of two or more dibenzoylmethane sunscreen compounds can be used. Exact amounts of the dibenzoylmethane sunscreen compound will vary depending upon the Sun Protection Factor, i.e. the "SPF" of the composition that is sought SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See *Federal Register*, Vol. 43, No. 166, pp. 38206–38269, Aug. 25, 1978, which is incorporated herein by reference in its entirety. Also, the desired level of UVA protection will also determine the exact amount of the dibenzoylmethane sunscreen compound to be used.

The dibenzoylmethane sunscreen compounds of the present invention comprise the dibenzoylmethane chromophore which can be represented by the following chemical structure.

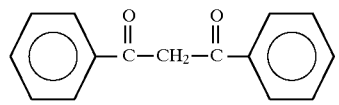

Even though the dibenoyzlmethane chromophore is represented above as a 1,3-diketone, it should be understood that this representation in no way excludes other tautomeric forms of the chromophore such as the enol form. Thus, whenever the 1,3-diketone form is designated, it is understood that all appropriate enol tautomers and other contributing structures are also contemplated and included herein. For example, the tautomeric enol forms of the dibenozylmethane chromophore can be represented by the following tautomeric structures.

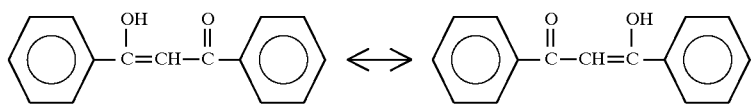

Dibenzoylmethane sunscreen compounds corresponding to the following chemical structure are useful in the present invention. Again, it is recognized that all appropriate tautomers are contemplated, though not explicitly represented.

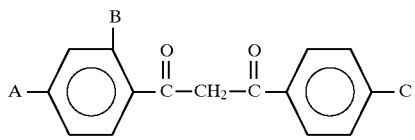

In the preceding chemical structure, A is a substituent selected from the group consisting of H, —OR, and —NR$_2$, wherein each R is independently selected from the group consisting of H, or straight or branched chain alkyl having from about 1 to about 20 carbon atoms, preferably wherein each R is independently selected from the group consisting of H, or straight or branched cahin alkyl having from about 1 to about 10 carbon atoms, more preferably wherein each R is independently selected from the group consisting of H, or straight or branched chain alkyl having from about 1 to about 4 carbon atoms; B is a substituent selected from the group consisting of H and —OH; and C is a substituent selected from the group consisting of H, or straight or branched chain alkyl having from about 1 to about 20 carbon atoms, preferably C is selected from the group consisting of H, or straight or branched chain alkyl having from about 1 to about 10 carbon atoms, more preferably C is selected from the group consisting of straight or branched chain alkyl having from about 1 to about 6 carbon atoms.

Dibenzoyl sunscreen compounds are described in U.S. Pat. No. 4,489,057, to Welters et al., issued Dec. 18, 1984 and U.S. Pat. No. 4,387,089, to DePolo, issued Jun. 7, 1983, both of which are incorporated by reference herein in their entirety. Nonlimiting examples of dibenzoylmethane sunscreen compounds corresponding to the previous chemical structure include those selected from the group consisting of 4,4'-methoxy-t-butyldibenzoylmethane, 4-isopropyldibenzoylmethane, 4-methoxydibenzoylmethane, 2,4'-hydroxy-t-butyldibenzoylmethane, 2,4,4'-hydroxymethoxy-t-butyldibenzoylmethane, and mixtures thereof. Preferred are 4,4'-methoxy-t-butyldibenzoylmethane, 4-isopropyldibenzoylmethane, and mixtures thereof. More preferred is 4,4'-methoxy-t-butyldibenzoylmethane.

The sunscreen 4,4'-methoxy-t-butyldibenzoylmethane, which is also known as butyl methoxydibenozylmethane, is commercially available under the trademark Parsol® 1789 from Givaudan Corporation. See *CTFA International Cosmetic Ingredient Dictionary*, fifth edition, 1993, p. 79, which is incorporated by reference herein in its entirety. The sunscreen 4-isopropyldibenzoylmethane, which is also known as isopropyl dibenzoylmethane, is commercially available under the trademark Eusolex® 8020 from Merck. See *CTFA International Cosmetic Ingredient Dictionary*, fifth edition, 1993, pp. 347–348, which is incorporated by reference herein in its entirety.

Other classes of dibenzoylmethane sunscreen compounds useful herein include those described in detail in U.S. Pat. No. 5,160,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20, 1991; U.S. Pat. No. 4,999,186, to Sabatelli et al., issued Mar. 12, 1991; and U.S. Pat. No. 4,937,370, to Sabatelli, issued Jun. 26, 1990; all of these patents being incorporated by reference herein in their entirety. These dibenzoylmethane sunscreen compounds comprise a dibenzoylmethane chromophore that is linked via a covalent bond to a second chromophore which can be selected from a wide variety of structures. Nonlimiting examples of these dibenozylmethane sunscreens are those selected from the group consisting of the ester formed from 4-N,N(2-ethylhexyl)methylaminobenzoic acid and 2-hydroxy-4(2-hydroxyethoxy)benzophenone, the ester formed from 4-N,N-dimethylaminobenzoic acid and 4-hydroxydibenzoylmethane, the ester formed from 4-N,N-dimethylaminobenzoic acid and 4-(2-hydroxyethoxy) dibenzoylmethane, the ester formed from 4-N,N-di(2-ethylhexyl)aminobenzoic acid and 4-hydroxydibenzoylmethane, the ester formed from 4-N,N-di(2-ethylhexyl)aminobenzoic acid ester and 4-(2-hydroxyethoxy)dibenzoylmethane, the ester formed from 4-N,N-2-ethylhexyl)methylaminobenzoic acid and 4-hydroxydibenzoylmethane, the ester formed from 4-N,N-(2-ethylhexyl)methylaminobenzoic acid ester and 4-(2-hydroxyethoxy)dibenzoylmethane, and mixtures thereof.

Surface-Treated Zinc Oxide

The compositions of the present invention comprise from about 0.1% to about 20%, preferably from about 0.5% to about 10%, and more preferably from about 1% to about 5% by weight of the composition of a surface treated zinc oxide. Exact amounts of the surface treated zinc oxide will vary depending upon the Sun Protection Factor, i.e. the "SPF" of the composition that is sought.

Zinc oxide can be represented by the chemical formula ZnO. It is generally a white or yellowish-white odorless powder. See The Merck Index, Tenth Edition, 1983, p. 1457, entry 9952, and International Cosmetic Ingredient Dictionary, Fifth Edition, 1993, pp. 788–789, both references being incorporated by reference herein in their entirety.

Surface-treated zinc oxide particles having a wide range of particle sizes can be used in the present invention. Preferred are those surface-treated zinc oxides having a mean particle size diameter from about 0.01 microns to about 100 microns, preferably from about 0.01 to about 10 microns, and more preferably from about 0.01 to about 2 microns. The surface-treated zinc oxides useful herein can be, but are not limited to, free-flowing powders and to pre-formed dispersions.

The particle size of the surface-treated zinc oxide particles of the present invention can be measured using a variety of different techniques well-known to the formulation scientist of ordinary skill in the art, e.g. laser diffraction, microscopy, filtration, sedimentation, etc. In the present invention, a preferred method of determining particle size is the laser diffraction technique using a commercially available laser particle size analyzer. In the present invention the particle size measurements are determined using a Horiba LA900 or 910 particle size analyzer (available from Horiba Instruments, Inc.). A variety of solvents of various viscosity and polarity can be used to disperse the particles in the samples to be analyzed for size. Preferred solvents include water and isopropanol, with isopropanol being more preferred.

The surface treatment materials used to surface treat the zinc oxide particles of the present invention can comprise from about 0.1% to about 50%, more preferably from about 0.25% to about 25%, and most preferably from about 0.5% to about 10% by weight of the surface-treated zinc oxide. Nonlimiting classes of surface treatment materials useful for treating the zinc oxide particles include silicones, fatty acids, proteins, peptides, amino acids, N-acyl amino acids, monoglycerides, diglycerides, triglycerides, mineral oils, silica, phospholipids, sterols, hydrocarbons, polyacrylates, alumina and mixtures thereof. Preferred herein is silicone-treated zinc oxide.

Examples of silicones useful as surface treatment material include dimethicone, methicone, cyclomethicone, dimethiconol, dimethicone copolyol, dimethicone copolyol acetate, dimethicone copolyol butyl ether, dimethicone copolyol methyl ether, and mixtures thereof. Also useful are fluorinated, phenyl-substituted, and amino-substituted derivatives of these silicones. Also useful are silicones having a reactive moiety which can chemically bond to the surface of the zinc oxide particle. Such zinc oxides having chemically bonded silicones and methods for their preparation are further described in U.S. Pat. No. 5,486,631, to Mitchnick et al., issued Jan. 23, 1996, which is incorporated herein by reference in its entirety. A particularly preferred zinc oxide for use in the present invention is prepared by the reaction of zinc oxide with a silicone compound having the following chemical structure.

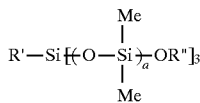

wherein R' is alkyl having from about 1 to about 10 carbon atoms; R" is selected from the group consisting of methyl or ethyl; and a is an integer ranging from about 4 to about 12.

Especially preferred for use herein is Z-Cote® HP1, hydrophobic microfine zinc oxide, which is commercially available from Sunsmart Inc., Wainscott, N.Y. This material is a zinc oxide that has been chemically reacted with a dimethicone material.

Examples of other surface treatment materials include the following:

Examples of fatty acids useful as surface treatment materials include $C_6$–$C_{30}$ straight or branched chain fatty acids, which can contain one or more unsaturated sites. Specific examples of fatty acids include capric acid, stearic acid, lauric acid, myristic acid, palmitic acid, oleic acid, ricinoleic acid, linoleic acid, linolenic acid, eleostearic acid, arachidonic acid, and mixtures thereof. Also useful herein are metal salts, i.e. soaps of these fatty acids. Useful metal salts of the fatty acids include sodium, potassium, magnesium, calcium, barium, aluminum, zinc, zirconium, titanium, and mixtures thereof.

Examples of proteins useful as surface treatment materials include collagen, chitin, casein, elastin, silk, and mixtures thereof. Examples of peptides include the partially hydrolyzed forms of the proteins just described wherein the proteins are broken down into a mixture of fragments each containing one or more amino acids.

Examples of amino acids useful as surface treatment materials include any of the naturally occurring amino acids, their N-methyl derivatives, and mixtures thereof. Also useful are salts of these materials. Preferred salts are those selected from the group consisting of aluminum, magnesium, calcium, zinc, zirconium, titanium, and mixtures thereof with aluminum being most preferred.

Examples of N-acyl amino acids useful as surface treatment materials include any of the amino acids, their N-methyl derivatives, or salts thereof just described, wherein the amino group has been acylated with a moiety derived from a $C_2$–$C_{30}$ straight or branched chain fatty acid.

Examples of mono-, di-, and triglycerides useful as surface treatment materials include those wherein the fatty acid portion of the molecule is derived from a $C_6$–$C_{30}$ straight or branched chain fatty acid.

Examples of mineral oils useful as surface treatment materials include mineral oil, petrolatum, and mixtures thereof.

An example of silica useful as a surface treatment material is fumed silica.

Examples of phospholipids useful as surface treatment materials include lecithin (which is also known as phosphatidyl choline), phosphatidyl ethanolamine, phosphatidyl serine, phosphatidyl inositol, phosphatidyl acid, and mix thereof.

Examples of sterols useful as surface treatment materials include cholesterol and cholesterol esters wherein the acid portion of the ester is derived from a $C_2$–$C_{30}$ straight or branched chain fatty acid.

Examples of hydrocarbons useful as surface treatment materials include polyethylene, polypropylene, polyisobutylene, squalane, squalene, and mixtures thereof. Also useful are fluorinated derivatives of polyethylene, polypropylene, and polyisobutylene.

Examples of polyacrylates useful as surface treatment materials include polyacrylic acid, polymethacrylic acid, polyethacrylic, and mixtures thereof.

An example of alumina useful as a surface treatment material is boehmite.

Ratios

In preferred embodiments of the present invention, the dibenzoylmethane sunscreen compound and the surface-treated zinc oxide are used within certain weight ratios. Preferably the weight ratio of the dibenzoylmethane sunscreen compound to the surface-treated zinc oxide is from about 10:1 to about 1:10, more preferably from about 6:1 to about 1:6, and most preferably from about 2:1 to about 1:6.

Carrier

The compositions of the present invention comprise a carrier, or vehicle, suitable for application to human skin. The exact amount of carrier will depend upon the level of the dibenzoylmethane sunscreen compound, the surface-treated zinc oxide, and any other optional ingredients which one of ordinary skill in the art would classify as distinct from the carrier. The compositions of the present invention comprise from about 20% to about 99.8%, preferably from about 50% to about 99%, and more preferably from about 75% to about 95%, by weight of the composition of a carrier.

The compositions of the present invention can be formulated into a wide variety of product types, including creams, lotions, milks, mousses, gels, oils, tonics, sprays, hand and body lotions, cold creams, facial moisturizers, anti-acne preparations, topical analgesics, makeups, lipsticks, and the like. The topical carrier and any additional components required to formulate such products vary with product type and can be routinely chosen by one skilled in the art.

The topical carrier can be in a wide variety of forms. For example, emulsion carriers, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurized aerosol containers using conventional propellants. These carriers can also be delivered in the form of a mousse. Other suitable topical carriers include aqueous-based single phase solvents, e.g., water, alcohols, glycols, polyols, and the like. Examples of topical carrier systems useful in the present invention are described in the following references, an of which are incorporated herein by reference in their entirety: "Sun Products Formulary," *Cosmetics & Toiletries*, vol. 105, pp. 122–139 (December 1990); "Sun Products Formulary," *Cosmetics & Toiletries*, vol. 102, pp. 117–136 (March 1987); U.S. Pat. No. 4,960,764 to Figueroa et al., issued Oct. 2, 1990; U.S. Pat. No. 4,254,105 to Fukuda et al., issued Mar. 3, 1981; U.S. Pat. No. 4,976,953, to Orr et al., issued Dec. 11, 1990; and U.S. Pat. No. 5,073,372, to Turner et al., issued Dec. 17, 1991.

Other forms of topical carriers are also useful. When the sunscreening composition is an aerosol spray or mousse, the carrier can also utilize any of the conventional propellants to deliver the material as a foam (in the case of a mousse) or as a fine, uniform spray (in the case of an aerosol). Examples of suitable propellants include materials such as trichlorofluoromethane, dichlorodifluoromethane, difluoroethane, dimethylether, propane, n-butane or isobutane. A more complete disclosure of propellants useful herein can be found in Sagarin, *Cosmetics Science and Technology*, 2nd Edition, Vol. 2, pp. 443–465 (1972), which is incorporated herein by reference in its entirety.

Suitable spray containers are well known in the art and include conventional, non-aerosol pump sprays, i.e., "atomizers," aerosol containers or cans having propellant, as described above, and also pump aerosol containers utilizing compressed air as the propellant. Pump aerosol containers are disclosed, for example, in U.S. Pat. Nos. 4,077,441, Mar. 7, 1978, Olofsson and 4,850,577, Jul. 25, 1989, both incorporated by reference herein, and also in U.S. Ser. No. 07/839,648, Gosselin, Lund, Sojka, and Lefebvre, filed Feb. 21, 1992, "Consumer Product Package Incorporating A Spray Device Utilizing Large Diameter Bubbles." Pump aerosols hair sprays using compressed air are also currently marketed by The Procter & Gamble Company under their tradename VIDAL SASSOON AIRSPRAY hair sprays.

The carriers useful herein often contain water. Typical water levels comprise from about 20% to about 99.8%, preferably from about 50% to about 99%, and more preferably from about 75% to about 95% by weight of the total composition.

Optional Ingredients
Additional Sunscreen Agents

The compositions of the present invention can optionally comprise additional sunscreen agents. These sunscreen agents can comprise from about 0.1% to about 30%, more preferably from about 0.5% to about 25%, and most preferably from about 1% to about 20% by weight of the compositions of the present invention. Exact amounts of sunscreen agent will vary depending upon the sunscreen or sunscreens chosen and the desired Sun Protection Factor (SPF) to be achieved.

A wide variety of additional sunscreen agents are useful herein. Nonlimiting examples of these sunscreen agents are described in U.S. Pat. No. 5,087,445, to Haffey et al., issued Feb. 11, 1992; U.S. Pat. No. 5,073,372, to Turner et al., issued Dec. 17, 1991; and U.S. Pat. No. 5,073,371, to Turner et al. issued Dec. 17, 1991; which are all incorporated by reference herein in their entirety. Preferred among the sunscreen agents are those selected from the group consisting of 2-ethylhexyl p-methoxycinnamate, octyl salicylate, octocrylene, oxybenzone, 2-ethylhexyl N,N-dimethylaminobenzoate, p-aminobenzoic acid, 2-phenylbenzimidazole-5-sulfonic acid, homomenthyl salicylate, DEA p-methoxycinnamate, 3-(4-methylbenzylidene) camphor, 3-benzylidene camphor, benzene-1,4-[bis(3-methylidenecamphormethylsulphonic)] acid, titanium dioxide, iron oxide, and mixtures thereof. It is well known to one of ordinary skill in the art that salt and acid-neutralized forms of the acidic sunscreens are also contemplated herein.

Artificial Tanning Agents

The compositions of the present invention can optionally comprise from about 0.1% to about 20%, more preferably from about 2% to about 7%, and most preferably from about 3% to about 6% of dihydroxyacetone as an artificial tanning agent.

Dihydroxyacetone, which is also known as DHA or 1,3-dihydroxy-2-propanone, is a white to off-white, crystalline powder. This material can be represented by the chemical formula $C_3H_6O_3$ and the following chemical structure.

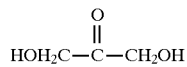

The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. Dihydroxyacetone is also known to be more stable at acidic pH values. See *The Merck Index*, Tenth Edition, entry 3167, p. 463 (1983), and "Dihydroxyacetone for Cosmetics", E. Merck Technical Bulletin, 03-304 110, 319 897, 180 588; both of these references being incorporated herein by reference in their entirety.

Crosslinked Polyacrylate Polymers

The compositions of the present invention can optionally comprise crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon—carbon double bond or other such polymerizable functional group, l is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternized, the polymers are preferably quaternized with short chain alkyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified. When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80. Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare® SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare® SC95. This polymer has recently been given the CTFA designation "Polyquaternium 37 (and) Mineral Oil (and) PPG-1 Trideceth-6". Another example of such a homopolymer is commercially available as a mixture containing the polymer, propylene glycol dicaprylate/dicaprate, and PPG-1 trideceth-6 as a dispersing aid, from Allied Colloids Ltd, (Norfolk, Va.) under the trademark Salcare® SC96. This polymer has the proposed CTFA designation "Polyquaternium 37 (and) propylene glycol dicaprylate/dicaprate (and) PPG-1 trideceth-6".

Polyacrylamide Polymers

The compositions of the present invention can optionally comprise polyacrylamide polymers, especially non-ionic polyacrylamide polymers including substituted branched or unbranched polymers. These polymers can be formed from a variety of monomers including acrylamide and methacrylamide which are unsubstituted or substituted with one or two alkyl groups (preferably $C_1$ to $C_5$). Preferred are acrylate amide and methacrylate amide monomers m which the amide nitrogen is unsubstituted, or substituted with one or two $C_1$ to $C_5$ allyl groups (preferably methyl, ethyl or propyl), for example, acrylamide, methacrylamide, N-methacrylamide, N-methylmethacrylamide, N,N-dimethylmethacrylamide, N-isopropylacrylamide, N-isopropylmethacrylamide, and N,N-dimethylacrylamide. These polymers have a molecular weight greater than about 1,000,000 preferably greater than about 1,5000,000 and range up to about 30,000,000. Most preferred among these polyacrylamide polymers is the non-ionic polymer given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

Humectants, Moisturizers, and Skin Conditioners

The compositions of the present invention can optionally comprise one or more humectant, moisturizing, or skin conditioning materials. A variety of these materials can be employed and each can be present at a level of from about 0.1% to about 20%, more preferably from about 1% to about 10%, and most preferably from about 2% to about 5%. These materials include guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol glycerol, hexanetriol propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof. Also useful herein are the propoxylated glycerols described in U.S. Pat. No. 4,976,953, to Orr et al., issued Dec. 11, 1990, which is incorporated by reference herein in its entirety.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305, 514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Emulsifiers

The compositions of the present invention can also comprise one or more emulsifiers. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof. The emulsifiers can be used individually or as a mixture of two or more and comprise from about 0.1% to about 10%, more preferably from about 0.15% to about 7%, and most preferably from about 0.25% to about 5% of the compositions of the present invention.

Other Optional Components

The compositions of the present invention can comprise a wide range of other optional components. These additional components should be pharmaceutically acceptable. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, absorbents, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, skin-conditioning agents (humectants, miscellaneous, and occlusive).

Some nonlimiting examples of these additional components cited in the *CTFA Cosmetic Ingredient Handbook* as well as other materials useful herein, include the following: vitamins and derivatives thereof (e.g. tocopherol, tocopherol acetate, retinoic acid, retinol, retinoids, and the like); polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; other anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; skin treating agents such as alpha-hydroxy acids such as lactic acid and glycolic acid, and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lace, witch hazel distillate, allantoin, bisabolol, and dipotassium glycyrrhizinate.

Methods for Protecting the Skin from UV Radiation

The compositions of the present invention are useful for providing protection to human skin from the harmful effects of UV radiation. To protect the skin a safe and effective amount of the composition is applied to the skin. By "safe and effective amount" is meant an amount effective for providing the benefits of the present invention, i.e. protection from the harmful effects of UV radiation, without any undue toxicity, allergic, or other unwanted side effects. By "protection" is meant that these compositions attenuate or reduce the amount of UV radiation reaching the skin's surface. Quantities of composition which are typically applied to provide protection are about, but not limited to, about 0.5 mg/cm$^2$ to about 25 mg/cm$^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Examples I–IV

| Ingredient | Photoprotective Compositions | | | |
|---|---|---|---|---|
| | I WT. % | II WT. % | III WT. % | IV WT. % |
| Phase A | | | | |
| Water | QS 100 | QS 100 | QS 100 | QS 100 |
| Glycerin | 6.0 | 3.0 | 3.0 | 6.0 |
| Disodium EDTA | 0.13 | 0.1 | 0.1 | 0.1 |
| Methylparaben | 0.25 | 0.25 | 0.25 | 0.25 |
| Phase B | | | | |
| Octylmethoxy Cinnamate | 7.5 | 4.0 | — | — |
| Silicone Coated Zinc Oxide[1] | 5.0 | 3.0 | 1.0 | 5.0 |
| Propylparaben | 0.15 | 0.15 | 0.15 | 0.15 |
| Steareth-2 | 0.15 | 0.15 | 0.1 | 0.15 |
| Steareth-21 | 1.35 | 1.35 | 0.9 | 1.35 |
| Cetyl Alcohol | 1.0 | 0.20 | 1.0 | 1.0 |
| Stearyl Alcohol | 1.0 | 0.60 | 1.0 | 1.0 |
| Behenyl Alcohol | 1.0 | 0.40 | 1.0 | 1.0 |
| C12–15 Alcohols Benzoate | 15.0 | 10.0 | 12.0 | 15.0 |
| DEA Oleth-3 Phosphate | 0.10 | 0.06 | 0.02 | 0.10 |
| 4,4'-methoxy-t-butyldibenzoyl-methane | 1.0 | 0.50 | 2.0 | 1.0 |
| Octocrylene | — | — | 1.5 | — |
| Phase C | | | | |
| Polyquaternium 37 (and) propylene glycol dica-prylate/dicaprate (and) PPG-1 trideceth-6[2] | 1.70 | — | — | 1.70 |
| Polyacrylamide (and) C13–14 isoparaffin (and) laureth-7[3] | — | 1.80 | 2.80 | — |
| Phase D | 0.50 | — | — | 0.50 |
| Benzyl Alcohol | | | | |

[1]Z-Cote ® HP1, hydrophobic microfine zinc oxide, which is commercially available from Sunsmart Inc., Wainscott, New York.
[2]Available as Salcare SC96 from Allied Colloids.
[3]Available as Sepigel 305 from Seppic Corporation.

The above compositions are prepared as follows:

Phase A, i.e. the water phase, is prepared by combining the indicated ingredients in an appropriate vessel with mixing and heating to 75° C. Phase B, i.e. the oil phase, is prepared by combining the indicated ingredients, except the surface-treated zinc oxide, in a separate vessel with mixing and heating to 75° C. Next the surface-treated zinc oxide is added to these Phase B ingredients with shearing. Next, the Phase B ingredients are mixed into the Phase A ingredients with shearing to form an emulsion. The resulting emulsion is cooled with mixing to 60° C. and the Phase C ingredient is added with mixing. The composition is cooled with mixing to 45° C. and the Phase D ingredient, when present, is added with mixing. The composition is then cooled to room temperature with mixing.

These compositions are useful for applying to human skin to provide protection from the harmful effects of UV radiation. These compositions demonstrate good UV absorbing efficiency, and good chemical, physical, and photostability.

What is claimed is:

1. A photoprotective composition useful for providing protection to human skin from the harmful effects of ultraviolet radiation, comprising:

(a) from about 0.1% to about 10% of a dibenzoylmethane sunscreen compound, (b) from about 0.1% to about 20% of a surface-treated zinc oxide having a mean particle size diameter from about 0.01 microns to about 100 microns, and (c) a carrier suitable for application to human skin.

2. A composition according to claim 1 wherein said dibenzoylmethane sunscreen compound and said surface-treated zinc oxide are present in a weight ratio of from about 10:1 to about 1:10.

3. A composition according to claim 1 wherein said dibenozylmethane sunscreen compound corresponds to the following chemical structure

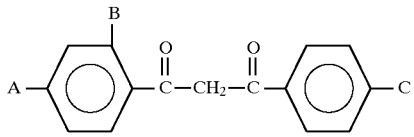

wherein A is a substituent selected from the group consisting of H, —OR, and —NR$_2$; wherein each R is independently H, or straight or branched chain alkyl having from about 1 to about 20 carbon atoms; B is a substituent selected from the group consisting of H and —OH; and C is a substituent selected from the group consisting of H, or straight or branched chain alkyl having from about 1 to about 20 carbon atoms.

4. A composition according to claim 3 wherein said surface-treated zinc oxide is surface treated with a material selected from the group consisting of silicones, fatty acids, proteins, peptides, amino acids, N-acyl amino acids, monoglycerides, diglycerides, triglycerides, mineral oils, silica, phospholipids, sterols, hydrocarbons, polyacrylates, alumina, and mix thereof.

5. A composition according to claim 4 wherein said surface-treated zinc oxide is surface treated with a silicone.

6. A composition according to claim 5 wherein said surface-treated zinc oxide is prepared by the reaction of zinc oxide with a silicone compound having the following chemical structure

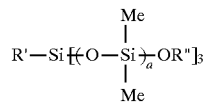

wherein R' is alkyl having from about 1 to about 10 carbon atoms; R" is methyl or ethyl; and a is an integer ranging from about 4 to about 12.

7. A composition according to claim 6 wherein said dibenzoylmethane sunscreen compound is selected from the group consisting of 4,4'-methoxy-t-butyldibenzoylmethane, 4-isopropyldibenzoylmethane, and mixtures thereof.

8. A composition according to claim 6 wherein said dibenzoylmethane sunscreen compound is 4,4'-methoxy-t-butyldibenzoylmethane.

9. A composition according to claim 7 wherein said composition further comprises from about 0.1% to about 30% by weight of the composition of an additional sunscreen agent selected from the group consisting of 2-ethylhexyl p-methoxycinnamate, octyl salicylate, octocrylene, oxybenzone, 2-ethylhexyl N,N-dimethylaminobenzoate, p-aminobenzoic acid, 2-phenylbenzimidazole-5-sulfonic acid, homomenthyl salicylate, DEA p-methoxycinnamate, 3-(4-methylbenzylidene) camphor, 3-benzylidene camphor, benzene-1,4-[bis(3-methylidenecamphormethylsulphonic)] acid, titanium dioxide, iron oxide, and mixtures thereof.

* * * * *

UNITED STATES PATENT AND TRADEMARK OFFICE
CERTIFICATE OF CORRECTION

PATENT NO. : 5,827,508

DATED : October 27, 1998

INVENTOR(S) : Paul Robert Tanner et al.

It is certified that error appears in the above-identified patent and that said Letters Patent is hereby corrected as shown below:

At column 1, line 56 "chemical physical and" should read --chemical, physical, and--.

At column 2, lines 3-4 "chemical physical" should read --chemical, physical--.

At column 2, line 22 "UVA protection" should read --UV protection--.

At column 3, line 9 "consist or" should read --consist of--.

At column 3, line 10 "or, the" should read --of, the--.

At column 3, line 36 "UVA absorbing" should read --UV absorbing--.

At column 4, line 29 "sought SPF" should read --sought. SPF--.

At column 6, line 6 "2-hydroxy-4(2-hydroxyethoxy)" should read --2-hydroxy-4-(2-hydroxyethoxy)--.

At column 6, line 15 "4-N,N-2-ethylhexyl)" should read --4-N,N-(2-ethylhexyl)--.

At column 7, line 5 "material" should read --materials--.

At column 7, lines 59-60 "thereof with" should read --thereof, with--.

At column 8, line 11 "and mix" should read --and mixtures--.

At column 9, line 3 "an of which" should read --all of which--.

At column 13, line 7 "trideceth-6"." should read --trideceth-6.--.

At column 13, line 16 "monomers m which" should read --monomers in which--.

At column 13, line 18 "allyl groups" should read --alkyl groups--.

At column 13, lines 47-48 "sorbitol glycerol" should read --sorbitol, glycerol--.

At column 13, line 48 "hexanetriol propylene" should read --hexanetriol, propylene--.

At column 13, line 62 "fatly acids" should read --fatty acids--.

At column 13, line 67 "fatly acids" should read --fatty acids--.

UNITED STATES PATENT AND TRADEMARK OFFICE
CERTIFICATE OF CORRECTION

PATENT NO. : 5,827,508
DATED : October 27, 1998
INVENTOR(S) : Paul Robert Tanner et al.

It is certified that error appears in the above-identified patent and that said Letters Patent is hereby corrected as shown below:

At column 15, line 8 "*Handbook* as" should read --*Handbook*, as--.

At column 15, line 28 "menthyl lace" should read --menthyl lactate--.

At column 17, line 24 "mix thereof" should read --mixtures thereof--.

Signed and Sealed this

Twenty-third Day of March, 1999

Attest:

Attesting Officer

Q. TODD DICKINSON

Acting Commissioner of Patents and Trademarks